United States Patent [19]
Oltra et al.

[11] Patent Number: 5,498,408
[45] Date of Patent: Mar. 12, 1996

[54] ORAL REHYDRATION COMPOSITION

[75] Inventors: Maria T. B. Oltra, Barcelona, Spain; Wolfgang Ernstberger, Laupen, Switzerland; Montserrat B. i Molas, Barcelona, Spain

[73] Assignee: Sandoz Nutrition Ltd., Berne, Switzerland

[21] Appl. No.: 223,070

[22] Filed: Apr. 4, 1994

Related U.S. Application Data

[63] Continuation of Ser. No. 948,376, Sep. 21, 1992, abandoned.
[51] Int. Cl.⁶ ................................................ A61K 35/78
[52] U.S. Cl. .................... 424/78.01; 514/54; 514/58; 514/867
[58] Field of Search ............. 424/78.01; 514/54, 514/58, 867; 426/547, 590, 622, 648

[56] References Cited

U.S. PATENT DOCUMENTS 4,971,814  11/1990  Tomita et al. .
5,120,539   6/1992  Lebenthal .

FOREIGN PATENT DOCUMENTS 0459108  12/1991  European Pat. Off. .
9115199  10/1991  WIPO .

OTHER PUBLICATIONS

Sloven, et al., Journal of Pediatrics, vol. 116, No. 6, pp. 876–881 (Jun. 1990).

Lebenthal, et al., Journal of Pediatrics, vol. 118, No. 4, Part 2, (Apr. 1991) pp. S62–S71.

The Lancet, vol. 339, pp. 219–220 (Jan. 25, 1992).

*Primary Examiner*—Jeffrey Mullis
*Attorney, Agent, or Firm*—Robert S. Honor; Carl W. Battle

[57] ABSTRACT

The invention relates to an oral rehydration formula containing a conventional carbohydrate, rice flour and carrot powder as carbohydrate sources.

12 Claims, No Drawings

ORAL REHYDRATION COMPOSITION

This is a continuation of application Ser. No. 07/948,376, filed Sep. 21, 1992, now abandoned.

The present invention relates to oral rehydration formulae.

Although infant mortality due to diarrhoea has decreased greatly in the world during recent decades, diarrhoea continues to be an important health problem.

Diarrhea is usually defined as the excessive loss of liquid and electrolytes from the gastrointestinal tract. This occurs when the equilibrium between the two intestinal functions, absorption and secretion, is broken.

From the pathophysiological point of view, there are three types of infectious diarrhea: it may be of viral origin, may be due to an enterotoxin or to an invading microorganism in the intestinal mucus.

The following problems have to be solved in the treatment of acute diarrhoea:

dehydration by hypersecretion of water and/or decrease in the absorption of water;

intestinal malabsorption of nutrients increase in intestinal permeability, and therefore risk of passage of proteins through the mucus and risk of outbreak of allergy;

intestinal exudation with loss of mucus and proteins.

Of all these problems, the one which requires the most urgent solution is the risk of dehydration.

The required amount of rehydration will not depend on the aetiology of the diarrhea nor on the age of the patient, but on the degree of dehydration of the patient, which can be easily evaluated by the loss of weight.

The use of an oral rehydration formula designed specifically for each environment is suitable both for prevention and for treatment of dehydration due to diarrhea and other causes, such as fever, produced by illness, increase in perspiration, high exposure to sun or hot environment, intense movement (of babies), increase in saliva due to teething, work which involves a high loss of liquids (in adults).

It has now been found that particularly effective rehydration of a patient may be achieved by oral administration to the patient of a drink containing a conventional carbohydrate, rice flour and carrot powder as carbohydrate sources.

The invention accordingly provides an oral rehydration formula containing a conventional carbohydrate, rice flour and carrot powder as carbohydrate source together with sufficient $Na^+$ and $K^+$ electrolytes to replace the losses of said electrolytes.

The oral rehydration formula according to the invention is particularly suitable for the treatment of unweaned babies, although it may be used throughout infancy and by adults.

The rice flour is conveniently employed in pregelatinised form.

The carrots are conveniently lyophilized in powder form. The use of commercial preparations based on carrot allows to control the level of nitrites (which react to nitrates) and avoids the risk of metahaemoglobinaemia, which is present in the use of home-made preparations with this foodstuff for small unweaned babies (babies of less than 4 months).

The level of nitrites of the oral rehydration formula product is conveniently below 4 mg per 100 g product.

The weight ratio of rice flour: carrot (the latter preferably in powder form) can vary within wide ranges, e.g. from 5:1 to 1:5.

The use of rice flour and carrot powder as carbohydrate sources allows for a higher supply of carbohydrates than would be possible with a conventional carbohydrate alone, without significantly increasing the osmolarity of the drink when ready for use, i.e. after dissolution in water. The carrot powder contributes to the good flavour of the product and renders the use of additives (sweeteners) unnecessary, despite the presence of potassium which is known to be bitter in taste.

The term conventional carbohydrates as used herein relates to carbohydrates known to be suitable for use in an oral rehydration formula drink such as glucose polymers or maltodextrines, e.g. maltodextrine DE 25.

The weight ratio of carbohydrates originating from rice flour and carrots to conventional carbohydrates can vary within wide ranges and will conveniently be selected such that the drink solution is slightly hypotonic and the taste of the drink is pleasant. In general such results will be achieved when employing a weight ratio of carbohydrates originating from rice flour and carrots: conventional carbohydrates in the range of from 1:1 to 1:7, preferably from 1:2 to 1:5, e.g. 1:4.

The composition of the rehydration formula is conveniently selected such that it is slightly hypotonic when in drink form.

The osmolality of the drink will therefore preferably be below 300 mOsm per kg drink solution. The osmolarity of the drink will therefore conveniently lie in the range of 210 to 290, e.g. at 250, mOsm/liter drink solution.

The amount and type of carbohydrate sources employed will be selected such that 1 l drink solution supplies from 30 to 90 g, preferably from 50 to 70, e.g. 60, g. carbohydrates per liter.

In addition to the $Na^+$ and $K^+$ electrolytes, the oral rehydration formula will conveniently contain a base to correct metabolic acidosis. Bases suitable for that purpose are bicarbonate and, more preferably, citrate, e.g. in the form of trisodium citrate dihydrate.

The amount of electrolytes and base to be added will conveniently be selected such that adequate concentrations are obtained in the drink solution.

For $Na^+$ this concentration is conveniently in the range of 30 to 90 mEq per liter drink solution. In general it is indicated to supply a lower concentration, e.g. in the range of from 50 to 70 mEq per liter; however, diseases resulting in a high loss of Na, such as cholera, require the administration of higher Na concentrations, i.e. up to about 90 mEq per liter.

For $K^+$ this concentration is conveniently in the range of from 18 to 42 mEq, more particularly from 20 to 30, e.g. 25 mEq per liter.

A suitable concentration of citrate in view of the losses lies in the range of from 25 to 35 mEq per liter drink solution.

The supply of the chloride ion is also important i.a. to secure Na absorption to increase the transport of Na and of glucose.

A suitable concentration of chloride ion is between 30 and 90 mEq, e.g. 50 mEq, per liter drink solution, and will depend on the total content of $Na^+$, $K^+$ and other anions.

The drink solution will conveniently contain carbohydrates in an amount supplying from 120 to 360, e.g. 200 to 280, KCAL (i.e. 504 to 1512, e.g. 840 to 1176, KJ).

An example of a suitable oral rehydration formula is as follows:

EXAMPLE 1

| Ingredients per 100 g of product | |
|---|---|
| Maltodextrine[1] (DE 25) | 65.46 g |
| Pregelatinized rice flour | 13.40 g |
| Lyophilized carrot in powder form | 13.00 g |
| Trisodium citrate dehydrate | 3.90 g |
| Sodium chloride | 2.50 g |
| Potassium chloride | 1.74 g |
| Oral rehydration formula | 100.00 g |

[1] a mixture of maltodextrine Glucidex$^R$ DE12 and maltodextrine Glucidex$^R$ DE40

The oral rehydration formula may be obtained by mixing the mineral salt, grinding the resultant mixture, sieving the ground mixture and the remaining raw material and mixing the whole.

The product according to Example 1, comprises—according to analysis:

TABLE 1

| | 100 g product | 1 l of drink/solution[1] |
|---|---|---|
| Carbohydrates | 83.4 g | 80 mM (61.0 g) |
| thereof | | |
| - maltodextrine | 63.3 g | 54 mM |
| - glucose polymers originating from | | |
| - rice | 10.7 g | 26 mM |
| - carrot | 9.4 g | |
| Proteins (N × 6.25) | 2.5 g | 1.8 g |
| Fats | 0.3 g | 0.2 g |
| Electrolytes | | |
| sodium | 1.9 g | 60 mEq |
| potassium | 1.4 g | 25 mEq |
| chloride | 2.5 g | 50 mEq |
| citrate | 2.4 g | 28 mEq |
| Energy value | Kcal 346 | 252 Kcal |
| | KJ 1446 | 1060 KJ |
| Osmolarity mOsm/l Sol | | 250 |
| Osmolality mOsm/kgH20 | | 263 |

[1] containing 73.2 g product.

It will be appreciated that in the case of important losses of liquid due to for example excessive heat, fever, vomiting, more diluted drink solutions may be administered.

Thus, where for treatment of diarrhea 18.3 g of the product according to Example 1 may be dissolved in 250 ml water (i.e. the content of 1 feeding bottle), the same amount may be administered as a solution in 500 ml of water in severe cases of dehydration.

The quantity of beverage to be administered daily is accordingly i.a. dependent on the loss of liquid.

The following will give some guidance for the appropriate use of the oral rehydration formula of the invention with babies:

Stage 1

In a first stage the degree of dehydration is determined, based on the loss of body weight:

| degree of dehydration | loss of weight |
|---|---|
| slight | 5% or less |
| moderate | 6–9% |
| severe | 10% or more |

(for severe dehydration without shock, oral rehydration is indicated; with shock the rehydration should be through the I.V. route).

Stage 2

During a first period of six hours and in case of moderate or severe dehydration, the baby is given 100 ml of the drink solution according to Table 1 per kg baby weight over a period of four hours and/or 50 ml of water per kg body weight over a period of two hours (or maternal mild "and libitum").

In case of slight dehydration, half of these volumes can be given.

Stage 3

The condition of the patient is re-evaluated after 6 hours.

If the rehydration as satisfactory normal feeding can be initiated.

If the rehydration was incomplete, the oral rehydration as stated under Stage 2 can be continued for another six hours.

If no improvement is observed, I.V. rehydration is indicated.

This and further treatment is in accordance with WHO recommended guidelines for treatment with oral rehydration drink solution.

We claim:

1. A formulated rehydration composition in powder form for oral administration consisting essentially of carbohydrates from rice flour, carrot powder, and conventional carbohydrates selected from the group consisting of maltodextrines, glucose polymers or mixtures thereof and electrolytes, wherein the weight ratio of rice flour to carrot powder in said composition ranges from 5:1 to 1:5, and the weight ratio of carbohydrates originating from rice flour and carrot powder to conventional carbohydrates ranges from 1:1 to 1:7, and wherein said composition supplies after dissolution in water a total amount per liter of from 30 to 90 g carbohydrates, from 30 to 90 m Equivalents of $Na^+$, from 18 to 42 m Equivalents of $K^+$, from 25 to 35 m Equivalents of citrate ions from trisodium citrate dihydrate, from 30 to 90 m Equivalents of $Cl^-$, and from 120 to 360 kcal/liter and has an osmolarity of from 210 to 290 mOsm/liter.

2. The composition of claim 1, wherein said carrot powder is in lyophilized powdered form.

3. The composition of claim 1, wherein said rice flour is in pregelatinized form.

4. The composition of claim 1 wherein the weight ratio of carbohydrates originating from rice flour and carrot powder to said conventional carbohydrates is in the range of from 1:2 to 1:5.

5. The composition of claim 1 wherein said composition supplies from 50 to 70 g carbohydrates per liter after dissolution in water.

6. The composition of claim 1 wherein said composition supplies from 50 to 70 mEq $Na^+$ per liter after dissolution in water.

7. The composition of claim 6, wherein said composition comprises from 20 to 30 mEq of $K^+$ per liter.

8. The composition of claim 7, wherein said composition comprises from 200 to 280 kcal per liter.

9. The composition of claim 1, wherein said carrot powder is in lyophilized powder form.

10. The composition of claim 9, wherein said rice flour is in pregelatinized form.

11. The composition of claim 9, wherein the weight ratio of carbohydrates originating from rice flour and carrot powder to said conventional carbohydrate is in the range of from 1:2 to 1:5.

12. The composition of claim 1 wherein said composition has been dissolved in water.

* * * * *